US012472345B2

(12) United States Patent
Sharma et al.

(10) Patent No.: US 12,472,345 B2
(45) Date of Patent: Nov. 18, 2025

(54) PULMONARY CIRCULATION ASSIST IMPLANT FOR A UNIVENTRICULAR HEART

(71) Applicant: AUFLOWS CARDIOTECH PVT LTD, Thane (IN)

(72) Inventors: Shailendra Deendayal Sharma, Thane (IN); Malay Suvagiya, Junagadh (IN)

( * ) Notice: Subject to any disclaimer, the term of this patent is extended or adjusted under 35 U.S.C. 154(b) by 485 days.

(21) Appl. No.: 18/099,907

(22) Filed: Jan. 20, 2023

(65) Prior Publication Data

US 2023/0381488 A1 Nov. 30, 2023

(30) Foreign Application Priority Data

May 26, 2022 (IN) ............................ 202221030169

(51) Int. Cl.

| | |
|---|---|
| ***A61M 60/148*** | (2021.01) |
| ***A61M 60/857*** | (2021.01) |
| *A61B 17/00* | (2006.01) |

(52) U.S. Cl.

CPC ........ *A61M 60/148* (2021.01); *A61M 60/857* (2021.01); *A61B 2017/00243* (2013.01)

(58) Field of Classification Search

None

See application file for complete search history.

(56) References Cited

U.S. PATENT DOCUMENTS

2011/0257462 A1* 10/2011 Rodefeld .................. A61F 2/06 600/16

2021/0154463 A1* 5/2021 Alexander .......... A61M 60/139

* cited by examiner

*Primary Examiner* — Jon Eric C Morales

(57) ABSTRACT

Embodiments herein provide a Pulmonary Circulation Assist Implant for passively regulating the cardiovascular blood flow in a subject born with a univentricular heart. The Pulmonary Circulation Assist Implant is configured to avoid a head-on collision between the bloodstreams from a Superior Vena Cava (SVC) and an Inferior Vena Cava (IVC) without an offset between them. Further, the Pulmonary Circulation Assist Implant is configured to smoothly distribute the SVC blood and IVC hepatic blood to both lungs in equal proportions without swirling. Also, the Pulmonary Circulation Assist Implant is configured to avoid the occurrence of retrograde flow and reduce power loss.

14 Claims, 15 Drawing Sheets

PULMONARY CIRCULATION ASSIST IMPLANT FOR A UNIVENTRICULAR HEART

RELATED APPLICATIONS

This application claims priority under 35 U.S.C. § 119 to IN Application 202221030169, filed May 26, 2022, such IN Application being incorporated by reference herein in its entirety.

FIELD

This invention relates to the field of biomedical engineering. Particularly, the present invention relates to Pulmonary Circulation Assist Implant and, more particularly, a Pulmonary Circulation Assist Implant for saving flow energy by reducing the momentum loss while proportionately diverting the blood flow to both lungs in a patient with a congenital heart defect (CHD) having a single functional ventricle. Specifically, the invention relates to Pulmonary Circulation Assist Implant for a univentricular heart.

BACKGROUND

In cases of univentricular CHD, it is imperative to surgically reroute the pulmonary circulation bypassing the heart to avoid deoxygenated blood mixing with oxygenated blood required for systemic circulation. It is particularly desirable to maintain normal blood circulation to the lungs and the body of the patient.

A diagram in FIG. 1A schematically depicts the natural circulation of blood in the human body. Deoxygenated blood returning from the entire body is received in the Right Atrium (RA) of the heart which supplies it to the Right Ventricle (RV). The RV further pumps the blood into the lungs for oxygenation from where it is received in the heart's Left Atrium (LA). The oxygenated blood from the LA is then received in the Left Ventricle (LV) which further pumps it to the entire body thus completing the closed circuit. The circulation of blood between the heart and the lungs is called pulmonary circulation and the one between the heart and the body is called systemic circulation.

FIG. 1B is a schematic diagram representing the blood circulation in the human body having congenital heart defect (CHD) with a single functional ventricle. In the case of CHD, the RV is malformed and both atria are interconnected through a hole (an atrial septal defect). As a result, the LV alone has to pump the mixture of the oxygenated blood and the deoxygenated blood to the lungs and the body both. Further, the blood from the lungs and the body returns to the LA and the RA, respectively to complete the circuit in two parallel closed loops.

In normal cardiovascular circulation, the blood flows in a single closed loop. RV and LV are anatomically separated by an intervening partition, called an interventricular septum. In this closed loop of cardiovascular flow, the ventricles are separated by the pulmonary and systemic vascular trees. When one of the ventricles is undeveloped, the functional ventricle has to pump the blood in both systemic and pulmonary vasculature. This results in two parallel loops.

The probability of children born with CHD having only one effective ventricle is about 40 per million births. In children with such birth defect, the single functional ventricle has to pump the blood simultaneously to the body as well as to the lungs, thereby performing both the pulmonary and the systemic circulations. This parallel circulation (across the pulmonary and systemic vascular network) causes cyanosis which is a result of the mixing of the oxygenated and the deoxygenated blood in the single ventricle. It also creates ventricular volume overload. Due to these reasons, children with one effective ventricle need to be treated to increase their life expectancy. For the palliation of this kind of severe congenital heart problem, a surgical anastomosis is performed which connects Superior Vena Cava (SVC) and Inferior Vena Cava (IVC) directly to the Right Pulmonary Artery (RPA) to create flow in series. This procedure is called Fontan operation.

The surgery termed "Total Cavo-Pulmonary Connection" (TCPC) is currently the most promising modification of a Fontan surgical repair (i.e., Fontan operation) for single ventricle CHD. The TCPC involves a surgical connection of the SVC and the IVC directly to the RPA, bypassing the right heart. The part of the RPA which remains left to the SVC and IVC after the anastomosis is now referred to as LPA. In the univentricular system, the ventricle experiences a workload that may be reduced by optimizing the cavae-to-pulmonary anastomosis. This palliative surgical procedure leads to a separation between the oxygenated and the deoxygenated blood, which is critical for effective oxygen transport to the human body. As a result of this modified blood circulation, the single ventricle experiences an increased workload, pumping the blood to both the body and the lungs.

The Fontan procedure involves correcting the congenital heart defect, wherein the right heart is completely bypassed from the blood circulation circuit, thereby preventing the mixing of the oxygenated blood with the deoxygenated blood and also rendering the circulation circuit in a single close loop. However, in the absence of the RV, the blood supply from the body to the lungs becomes a passive process and hence suffers from kinetic energy loss. The blood circulation in the human body after a Fontan surgery is schematically shown in FIG. 1C.

FIG. 2A schematically illustrates the sectional anatomy of a normal heart wherein all major vital parts are shown. In contrast, the schematic in FIG. 2B shows a case of CHD wherein the RV is undeveloped and the tricuspid valve is stenosed. The atrial septal defect lets the deoxygenated blood from the RA to the LA containing the oxygenated blood, and then their mixture is pumped by the single functioning ventricle to the entire body including the lungs.

The TCPC surgery is one of the variants of the Fontan operation which is in a simple form of a cross-connection as shown in FIG. 3A. As a result of this TCPC surgery, the bloodstreams flowing in opposite directions through the SVC and the IVC collide head-on with each other and lose momentum thereby causing the loss of kinetic energy. In addition, undesirable turbulence and swirl are also created due to the collision between these bloodstreams.

A method to minimize the impact of the collision between the SVC and the IVC bloodstreams exists by providing an offset between the SVC and IVC axes, as shown in FIG. 3B. Consequently, a vortex gets formed due to shear between the opposite bloodstreams. This vortex facilitates the smooth flow of blood to the lungs; however, it absorbs a little energy from the bloodstreams to sustain its rotation. This energy loss caused by the vortex formation is still less compared to the head-on collision of the bloodstreams.

However, this surgical offset leads to lung developmental problems caused due to unequal IVC blood flow distribution. For example, depending on the extent of the offset, the bloodstreams choose their paths and create a bias for the IVC blood towards one of the lungs, thereby depriving the other lung of sufficient nutritive secretion that is provided by hepatic veins in the liver to the IVC blood. Deprivation of this hepatic content renders the blood incapable of absorbing oxygen from the air in the lung and releasing carbon dioxide, which eventually leads to pulmonary arteriovenous malformation (PAVM) in the lung as depicted by the image in FIG. 3C.

SUMMARY

A principal object of the embodiments herein is to provide a Pulmonary Circulation Assist Implant for avoiding the offset in a TCPC surgery, yet passively regulating bloodstreams in a subject.

Another object of the embodiments herein is to provide a Pulmonary Circulation Assist Implant for passively regulating bloodstreams with reduced turbulence and swirl in a subject.

Another object of the embodiments herein is to provide the Pulmonary Circulation Assist Implant for separating a bloodstream from the IVC and a bloodstream from the SVC, without a collision between the bloodstreams.

Another object of the embodiments herein is to provide the Pulmonary Circulation Assist Implant for distributing the bloodstream from the IVC in proportion to the LPA and the RPA.

Another object of the embodiments herein is to provide the Pulmonary Circulation Assist Implant for distributing the bloodstream from the SVC in proportion to the LPA and the RPA.

Another object of the embodiments herein is to provide the Pulmonary Circulation Assist Implant for eliminating the retrograde flow occurring due to a head-on collision between the SVC and the IVC bloodstreams having different velocities.

Yet another object of the embodiments herein is to provide the Pulmonary Circulation Assist Implant for appropriately diverting the IVC blood carrying hepatic contents to both the lungs depending on the impedance offered by each pulmonary vascular tree.

Yet another object of the embodiments herein is to provide the Pulmonary Circulation Assist Implant to merge two separated streams and allow a co-flow with minimal spiraling and reduced shear between the streams at the interface.

Accordingly, the embodiments herein provide a Pulmonary Circulation Assist Implant for passively regulating bloodstreams in a subject having CHD with a univentricular heart. The Pulmonary Circulation Assist Implant is configured to separate a bloodstream from an IVC and a bloodstream from an SVC to circumvent collision between the bloodstreams without providing an offset. Further, the Pulmonary Circulation Assist Implant is configured to distribute the bloodstream from the IVC in proportion to an LPA and an RPA. Further, the Pulmonary Circulation Assist Implant is configured to distribute the bloodstream from the SVC in proportion to the LPA and the RPA.

In an embodiment, the Pulmonary Circulation Assist Implant regulates the bloodstream from the IVC in proportion to the LPA and the RPA without artificial constraint.

In an embodiment, the Pulmonary Circulation Assist Implant regulates the bloodstream from the SVC in proportion to the LPA and the RPA without artificial constraint.

In an embodiment, the Pulmonary Circulation Assist Implant is further configured to merge the bloodstream from the SVC and the IVC through the LPA and the RPA without artificial constraint.

In an embodiment, the Pulmonary Circulation Assist Implant is constructed using biocompatible materials.

In an embodiment, the Pulmonary Circulation Assist Implant possesses compliant property similar to the native vena-cava and pulmonary artery for ease of anastomosis.

According to this invention, there is provided a Pulmonary Circulation Assist Implant configured to separate bloodstream from an IVC and bloodstream from an SVC to circumvent collision between the bloodstreams without providing an offset, said implant comprising:

- a long conduit crossing an operative transverse short conduit with a junction being formed at said crossing, said long conduit and said short conduit forming a cross,
- said long conduit having a first open long end and a second open long end, with said junction therebetween, said first open long end being configured to be anastomosed with a Superior Vena Cava (SVC), said second open long end being configured to be anastomosed with an Inferior Vena Cava (IVC);
- said short conduit having a first open short end and a second open short end, with said junction therebetween, said first open short end being configured to be anastomosed with a Left Pulmonary Artery (LPA), said second open short end being configured to be anastomosed with a Right Pulmonary Artery (RPA); and
- a flow manipulator being provided at said junction, said flow manipulator configured to, smoothly, regulate blood flows from said Superior Vena Cava (SVC) and said Inferior Vena Cava (IVC) to said Left Pulmonary Artery (LPA) and said Right Pulmonary Artery (RPA), respectively, by forming four distinct quadrants, for smooth curvilinear flows of blood streams entering through said ends of said long conduit and exiting through said ends of said short conduit.

In at least an embodiment, said implant being made of compliant and biocompatible materials having long term hemocompatibility properties.

In at least an embodiment, said long conduit, having a diameter between 18 and 20 mm, forming a prosthetic extension of said Inferior Vena Cava (IVC).

In at least an embodiment, said first open short end and a second open short end being sized in the range (10 to 16 mm) of said Right Pulmonary Artery (RPA) diameter.

In at least an embodiment, said first open long end being sized in the range (10 to 16 mm) of said Superior Vena Cava (SVC) diameter.

In at least an embodiment, said second open long end being larger in diameter than said first open long end.

In at least an embodiment, said flow manipulator being a stiff flat element having a smooth surface finish, said flow manipulator being positioned in a plane defined by a locus of points formed by a spaced apart region between:

- a centre plane defined across a flow axis, of said short conduit; and
- 0.1 times the diameter of said second open long end.

In at least an embodiment, said flow manipulator being a stiff flat element having a smooth surface finish, said flow manipulator being positioned in a plane defined by a locus of points formed by a spaced apart region between:

- a centre plane defined across a flow axis, of said short conduit; and
- 0.1 times the diameter of said second open long end,
- in that, said flow manipulator being positioned, offset, operatively towards said first open long end.

In at least an embodiment, said flow manipulator spans said junction wherein operative lateral sides of said flow manipulator connect normally with inner curved opposite walls in order to hold said flow manipulator, in position, making two longitudinal corners within said formed junction of said implant.

In at least an embodiment, said flow manipulator spans said junction wherein operative end free trailing edges of said flow manipulator extending, covering fully, projected opening of said ends, and facilitating merging and coflowing of streams from said Superior Vena Cava (SVC) and from said Inferior Vena Cava (IVC) flowing through said Left Pulmonary Artery (LPA) and said Right Pulmonary Artery (RPA).

In at least an embodiment, width of said flow manipulator matches diameter of said second open long end.

In at least an embodiment, joints of said junction of said long conduit and said short conduit are rounded off to render curved corners for smooth turning of flows, at said junction, caused by said flow manipulator, without separation.

In at least an embodiment, axis of said short conduit being a curvilinear axis matching a patient's Right Pulmonary Artery (RPA).

In at least an embodiment, axis of said short conduit being a non-planar curvilinear axis matching a patient's Right Pulmonary Artery (RPA).

These and other aspects of the embodiments herein will be better appreciated and understood when considered in conjunction with the following description and the accompanying Figures. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

This invention is illustrated in the accompanying drawings; throughout which reference letters indicate corresponding parts in the various figures. The embodiments herein will be better understood from the following description with reference to the drawings, in which:

FIG. 1A pulmonary and systemic circulations representing normal physiology, FIG. 1B congenital heart defect depicting univentricular physiology, and FIG. 1C Fontan physiology wherein the pulmonary circulation bypasses the right heart that includes non-functional right ventricle (RV) and the pairing right atrium (RA);

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The embodiments herein provide a Pulmonary Circulation Assist Implant for automatically, and passively, regulating blood streams in a subject having a univentricular heart. The Pulmonary Circulation Assist Implant is configured to separate a bloodstream from an Inferior vena cava (IVC) and a bloodstream from a Superior vena cava (SVC) in order to circumvent collision between the bloodstreams. Further, the Pulmonary Circulation Assist Implant is configured to distribute the bloodstream from the IVC in proportion to an left pulmonary artery (LPA) and a right pulmonary artery (RPA). Further, the Pulmonary Circulation Assist Implant is configured to distribute the bloodstream from the SVC in proportion to the left pulmonary artery (LPA) and the right pulmonary artery (RPA).

Figure 1A:
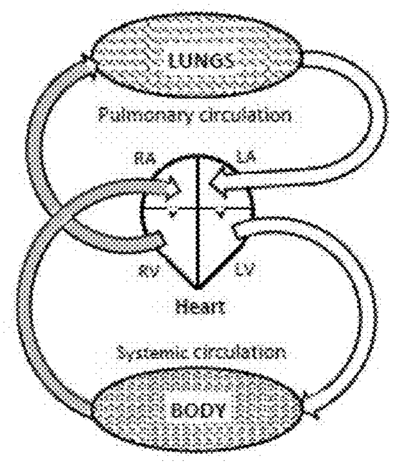
FIGS. 1A-C show schematic diagrams of hemodynamic circulation.
Figure 1B:
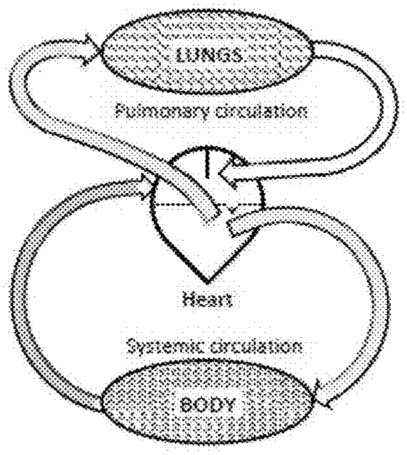
Figure 1C:
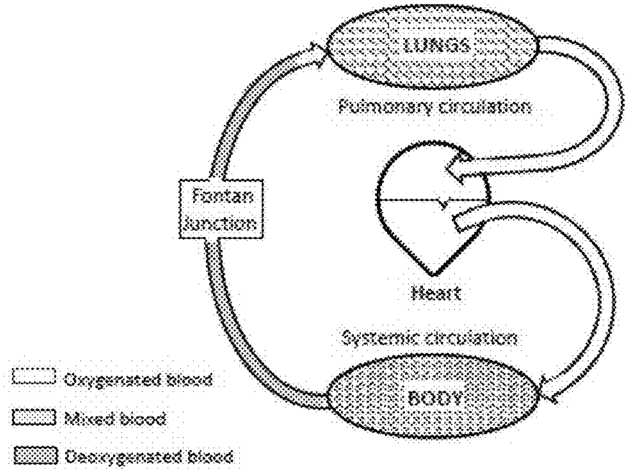
Figure 2A:
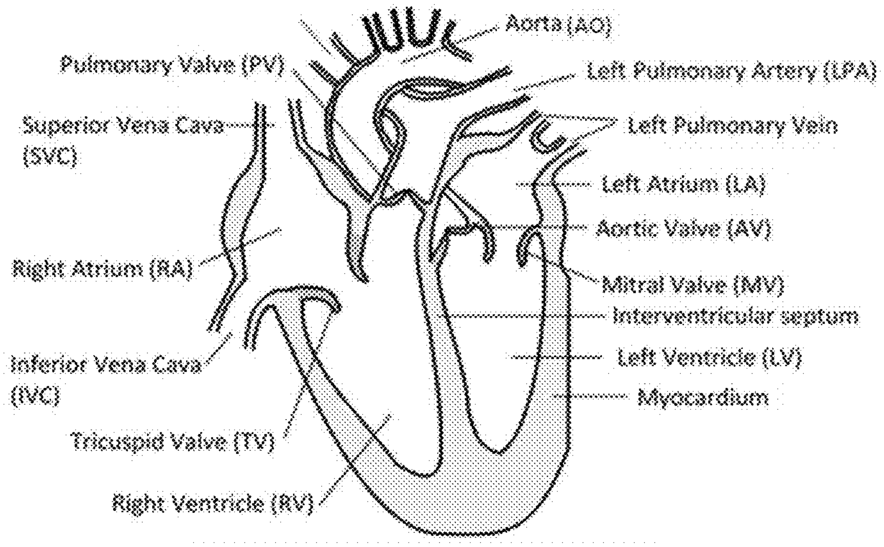
FIG. 2A is a schematic of the anatomy of a normal healthy heart.
Figure 2B:
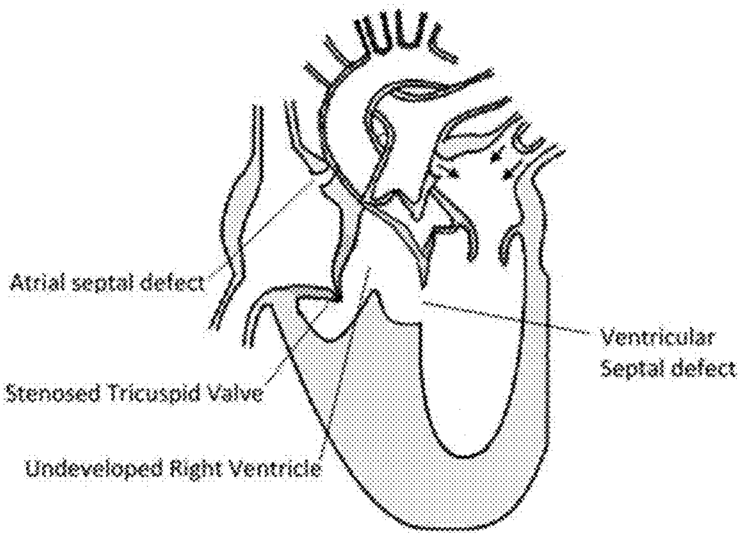
FIG. 2B is a schematic of the anatomy of a univentricular heart with a congenital defect showing a malformed right ventricle (RV) and stenosed tricuspid valve (TV)

A septum as seen in FIG. 2A divides the heart vertically into the left heart and right heart, and each of these is further horizontally divided into atrium and ventricle with a non-return valve between them. Thus, the heart has four chambers—Left Atrium (LA), Left Ventricle (LV), Right Atrium (RA), and Right Ventricle (RV). The RA receives deoxygenated blood through the SVC from the upper part of the body (head and arms) and through the IVC from the lower part of the body (torso and legs), respectively. The deoxygenated blood is then supplied through a Tricuspid Valve (TV) to the RV which further pumps it through Pulmonary Valve (PV) to the LPA and to the RPA leading to left and right lungs for oxygenation. The LA receives oxygenated blood from the lungs through Pulmonary Veins and pushes it through Mitral Valve (MV) into the LV. Impulsive contraction of the LV pumps the oxygenated blood through Aortic Valve (AV) to the highly curved Aorta whose branches supply the oxygenated blood to the upper part of the body and to the lower part of the body, thus completing the circuit of blood circulation. FIG. 2B schematically shows a typical congenital heart defect wherein the RV is malformed, TV is stenosed, and the atrial septal defect is present in the form of a hole between the RA and the LA. Such septal defect allows the mixing of oxygenated blood with deoxygenated blood. In this situation, the LV alone pumps the mixed blood simultaneously to the body and to the lungs thereby causing continual deterioration of the child's health warranting urgent surgical correction.

Fontan operation, which is a palliative procedure, is the most practiced surgical treatment that has undergone several modifications. The most recent modification involves disconnecting the SVC and the IVC from the RA of the heart and then anastomosing the SVC directly and the IVC through an extracardiac prosthetic conduit to the pulmonary artery to route the systemic venous blood to the pulmonary circulation. This variant of the Fontan operation is called total cavo-pulmonary connection (TCPC) which renders an anatomic configuration in the shape of a cross.

Figure 3A:
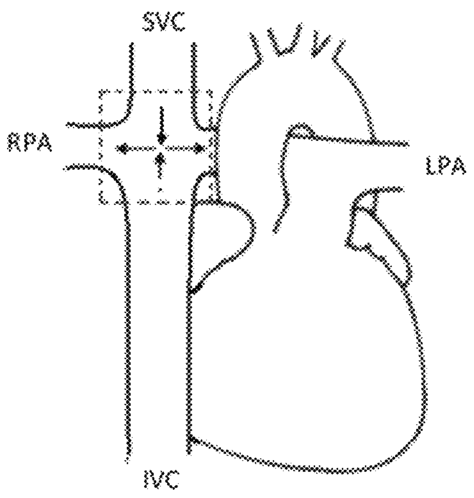
FIG. 3A depicts a schematic of total cavo-pulmonary connection (TCPC) wherein the superior vena cava (SVC) and inferior vena cava (IVC) are connected to the right pulmonary artery (RPA) facing each other.

The blood flow in the TCPC configuration with the co-axial (inline) SVC and IVC is depicted in a simplest possible representation of a TCPC junction with a flow pattern as shown in FIG. 3A. This configuration of the co-axial SVC and the IVC shows that flows from opposite directions collide within the pulmonary artery. This fluid-fluid interaction results in loss of momentum, generation of turbulence and swirling flows which get diverted orthogonally into the RPA and the LPA.

Figure 3B:
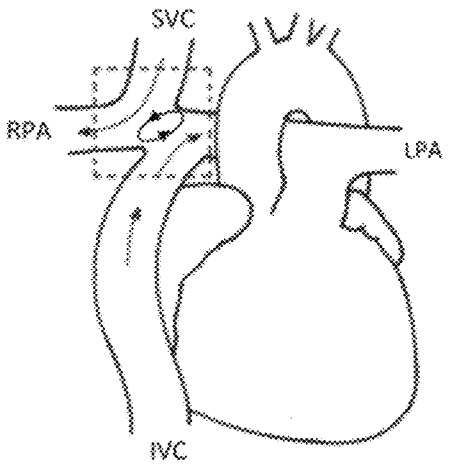
FIG. 3B depicts a schematic of total cavo-pulmonary connection (TCPC) wherein the superior vena cava (SVC) and inferior vena cava (IVC) are connected to right pulmonary artery (RPA) with an offset between them.
Figure 3C:
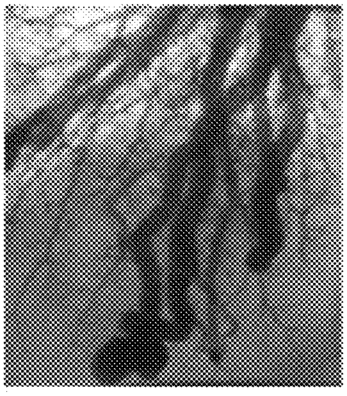
FIG. 3C is an image of pulmonary arteriovenous malformation (PAVM) in a lung.

In order to circumvent the problems caused by the co-axial SVC and the IVC, surgeons connect the SVC and IVC to the pulmonary artery with an offset as shown in FIG. 3B. The offset configuration has been found to reduce energy loss and therefore this is the currently prevalent surgical practice. The TCPC procedure, which restores the vital separation between oxygenated and deoxygenated blood, also leads to an increased workload for the remaining single ventricle, as it is now responsible for pumping the blood through both the systemic and pulmonary circulations. However, the offset results in disproportionate distribution of the IVC blood to the lungs owing to bias of the SVC blood flow towards the RPA and the IVC blood flow towards the LPA which is facilitated by a vortex emerging between these two streams. The bias of the IVC flow containing hepatic nutrients to one lung leads to pulmonary arteriovenous malformation (PAVM) in the other lung due to an insufficient supply of hepatic contents. Due to the PAVM, arteries and veins in a lung develop abnormal connections between them. Arteries carrying blood from the heart transport it to smaller arteries which then feed into much smaller capillaries residing in organs. These capillaries slow down the blood flow and allow for the hepatic nutrients and gas exchange between the blood and organs. Veins then transport the blood back from the capillaries to the heart. In a diseased lung due to the PAVM, the arteries and veins directly get connected without intervening capillaries forming bulges as can be seen in FIG. 3C. This abnormality results in reduced gas exchange and weak vascular walls thereby causing a decrease in oxygen levels and often bleeding into the lung. Thus, the blood flow from the IVC must be proportionately distributed to both lungs.

This invention's Pulmonary Circulation Assist Implant, unlike prior art systems and methods, enables a smooth and non-swirling flow of bloodstreams commencing from the SVC and the IVC, proportionately to the LPA and the RPA. As a result of reduced momentum, loss due to avoidance of fluid-fluid interaction (impingement of two opposite bloodstreams), the power loss in the blood flow is reduced thereby reducing the load on a ventricle.

Unlike the prior art mechanism, this invention's Pulmonary Circulation Assist Implant eliminates the need for an offset between the SVC and the IVC and directs the blood flow in proportionate quantity to both lungs.

Referring now to the drawings, and more particularly to FIG. 4, FIG. 5, FIG. 6, and FIG. 7, where similar reference characters denote corresponding features consistently throughout the figures, preferred embodiments are shown therein.

Figure 4:
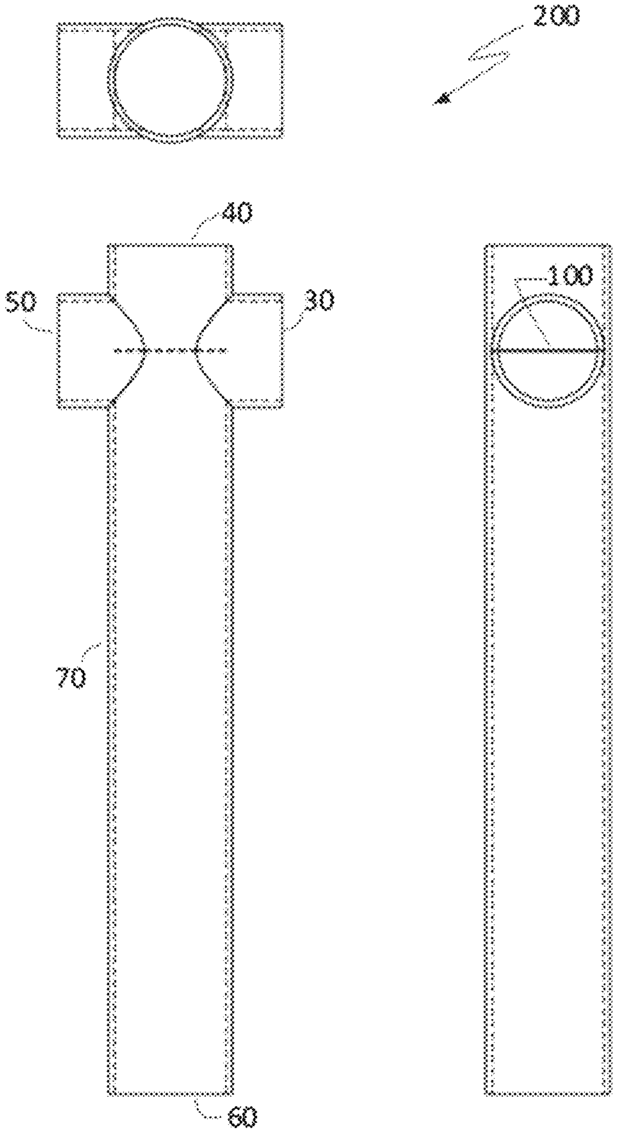
FIG. 4 depicts proportionate drawings of the present invention—Pulmonary Circulation Assist Implant (PCAI, 200). Ends 30, 40, 50, and 60 connect to Left Pulmonary Artery (LPA), Superior Vena Cava (SVC), Right Pulmonary Artery (RPA), and Inferior Vena Cava (IVC), respectively. 70 is a long conduit to join IVC and Pulmonary Artery (PA), and 100 is the flow manipulator.

FIG. 4 is a proportionate drawing of the present invention Pulmonary Circulation Assist Implant 200 showing three views. In at least an embodiment, the implant 200 is a tubular configuration, in the shape of a cross, housing a Flow Manipulator 100 in a junction. The Pulmonary Circulation Assist Implant 200 is constructed out of biocompatible materials having compliance similar to the pulmonary artery and venae cavae. In at least an embodiment, the flow manipulator 100 is provided at a junction, the junction being formed by a cross formed by a long conduit 70 crossing an operative transverse short conduit. Typically, the long conduit 70 has a first open long end 40 and a second open long end 60. Typically, the short conduit has a first open short end 30 and a second open short end 50. The open end 30 is to be anastomosed with the LPA, 40 with the SVC, 50 with the RPA, and 60 with the IVC. A long conduit 70, preferably, having a diameter between 18 and 20 mm, forms a prosthetic extension of the IVC. Open ends 30 and 50 are sized in the range (10 to 16 mm) of the RPA diameter, and another open end 40 is sized in the range (10 to 16 mm) of the SVC diameter depending on the age and/or body size of the patient.

In at least an embodiment, this Flow Manipulator 100, which is a stiff flat element having a smooth surface finish and thickness, preferably, in the range of 0.4 to 1.0 mm, is positioned in a plane defined by a locus of points, formed between the axis and 0.1 D above it towards the open end 40, where D is the diameter of the open end 60.

Figure 5:
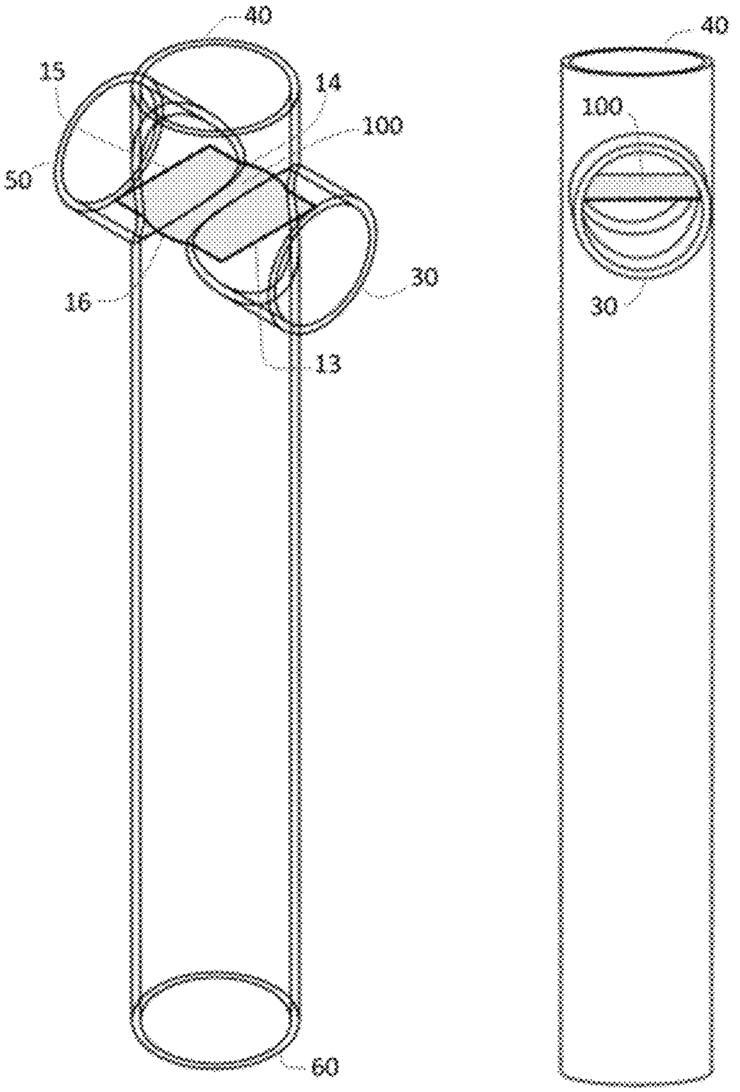
FIG. 5 illustrates three-dimensional views revealing geometric details of the present invention—Pulmonary Circulation Assist Implant (PCAI, 200)

FIG. 5 shows three-dimensional views from different angles for clarity about the geometry and shape of the present invention Pulmonary Circulation Assist Implant 200. The Flow Manipulator 100, shown shaded in grey, is the most critical component of the preferred embodiment which smoothly regulates the blood flows from the SVC and the IVC to the LPA and the RPA. Further, the Flow Manipulator 100 spans the TCPC junction wherein its sides 14 and 16 connect normally with the curved opposite walls and hold the flow manipulator 100 in position making two longitudinal corners within the formed junction of the Pulmonary Circulation Assist Implant 200. The straight free trailing edges 13 and 15 of the flow manipulator 100 extend covering fully the projected opening of the ends 40 and 60, and facilitate merging and coflowing of the SVC and IVC flows through LPA and RPA.

Figure 6:
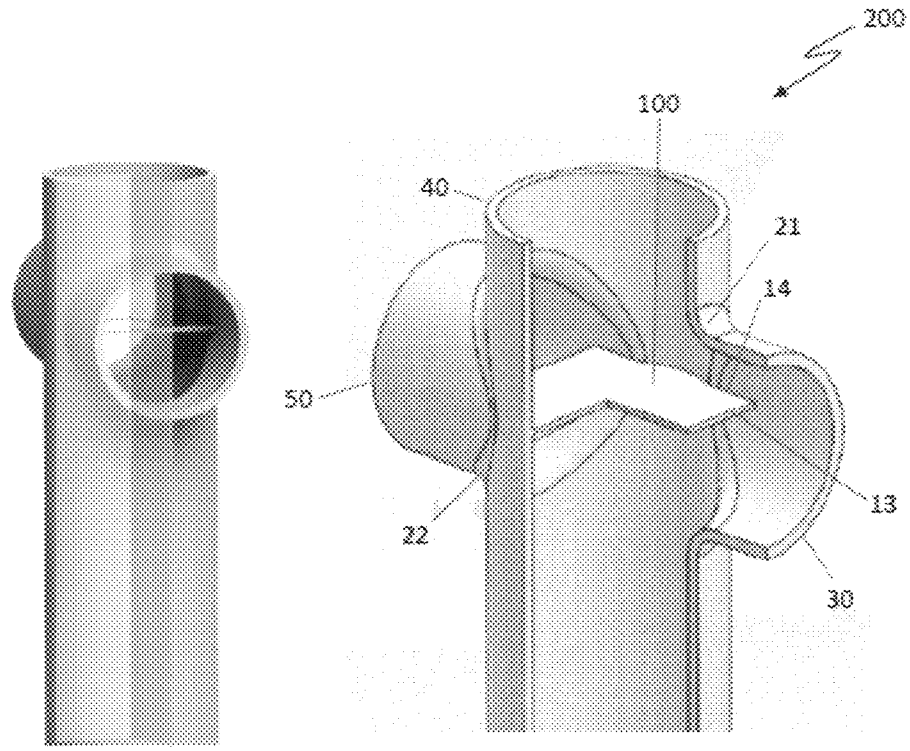
FIG. 6 shows a one-fourth-cut sectional view of the present invention (PCAI, 200) depicting its interior details including the placement of the flow manipulator 100 spanning the opposite walls of the junction, the PCAI 200 having rounded off joints of the junction rendering curved corners 21 and 22.

FIG. 6 is a quarter-sectional view of the present invention, Pulmonary Circulation Assist Implant 200, depicting interior architectural details of the junction and fitting of the flow manipulator 100 in the middle thereof. The joints of the junction of long conduit and short conduit are rounded off to render curved corners 21 and 22 for smooth turning of flows without separation.

Figure 7:
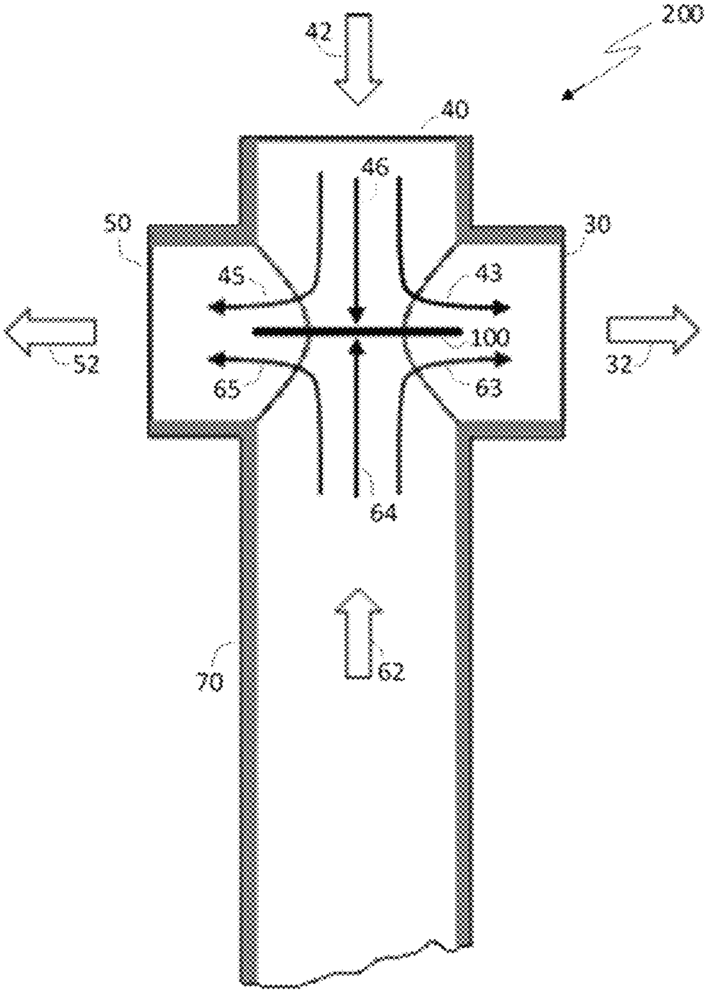
FIG. 7 shows a longitudinal cut-section of the present invention (PCAI, 200) with the labeling of flows: 42 and 62 are flows in from SVC and IVC, respectively; 32 and 52 are flows out to LPA and RPA, respectively; 46 and 64 are stagnation streamlines; 43 and 45 show flows from SVC deflected to LPA and RPA, respectively above the flow manipulator 100; similarly, 63 and 65 show flows from IVC deflected to LPA and RPA, respectively below the flow manipulator 100.

FIG. 7 depicts a longitudinal mid-sectional view of the Pulmonary Circulation Assist Implant 200 with some flowlines representing the flow pattern. 42 and 62 denote the net flows into the TCPC junction from the SVC and the IVC, respectively. 32 and 52 denote the net outflows from the TCPC junction to the LPA and the RPA, respectively. Flowlines 46 and 64 are the dividing streamlines impinging on the surfaces of Flow Manipulator 100 from the SVC and the IVC, respectively thereby representing the fluid-structure interaction. Thus, 46, 100, and 64 form the boundaries of the four quadrants in the TCPC junction which enable smooth turning of the flows from the SVC and the IVC. Streamlines 43 and 45 represent the SVC flow dividing about streamline 46 and smoothly turning into the LPA and the RPA, respectively. Similarly, streamlines 63 and 65 represent the IVC flow dividing about streamline 64 and smoothly turning into the LPA and the RPA, respectively. Accordingly, the figure elucidates pulmonary circulation facilitated by the preferred embodiment without the right ventricle (RV) being present.

Figure 8A:
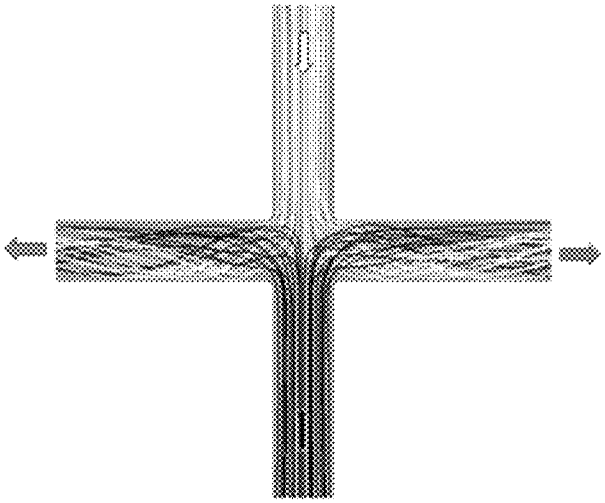
FIG. 8A shows the CFD simulation results displaying the streamlines for baseline TCPC configuration.
Figure 8B:
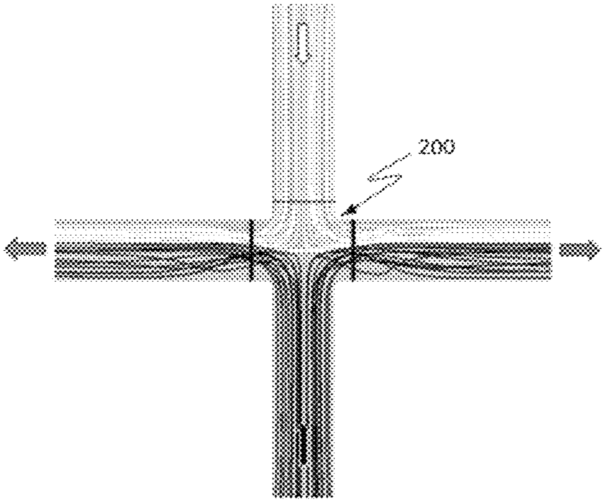
FIG. 8B shows the CFD simulation results displaying the streamlines for TCPC configuration formed using the present invention—Pulmonary Circulation Assist Implant (PCAI) 200. SVC and IVC flows share 30 and 70% of the cardiac output (CO) of 6 L/min in both cases.

FIG. 8A-B depicts three-dimensional flow patterns employing streamlines obtained through CFD simulation for the SVC flow rate of 1.8 L/min and the IVC flow rate of 4.2 L/min in the TCPC configuration. FIG. 8A illustrates intense interaction between the two flows from opposite directions resulting in strongly swirling flows in the LPA and the RPA. Whereas when the present invention, Pulmonary Circulation Assist Implant 200, is used to form the TCPC configuration as shown in FIG. 8B, the Flow Manipulator 100 prevents the interaction between the flows from the SVC and the IVC and allows them to smoothly co-flow in the LPA and the RPA without the swirl.

Figure 9:
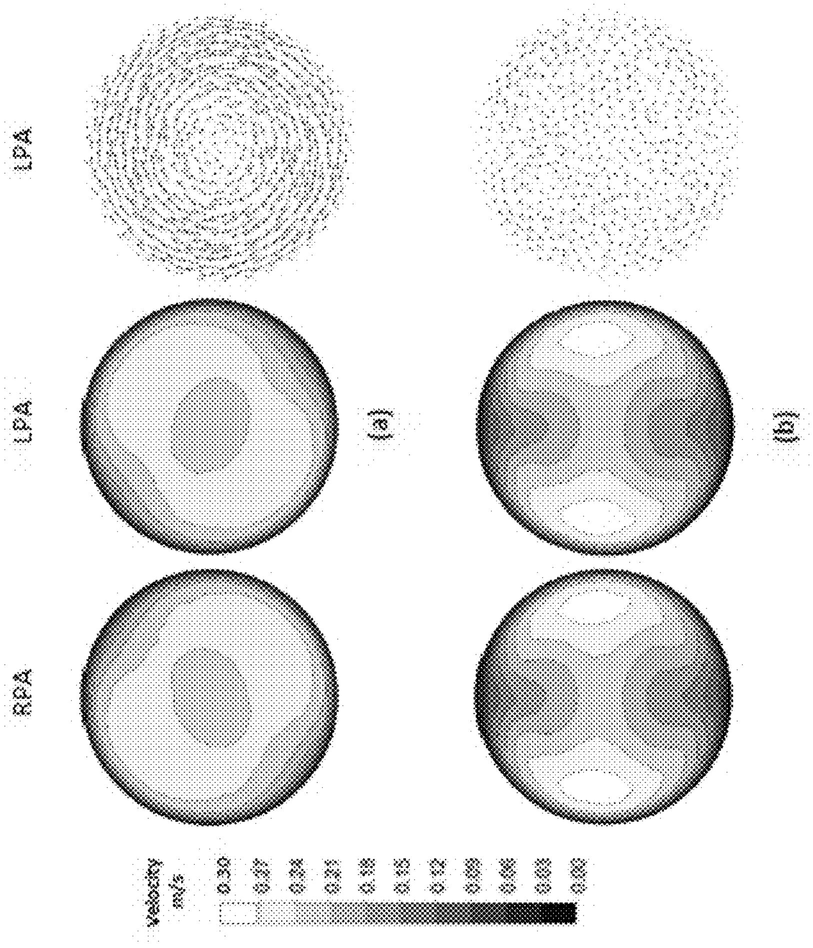
FIG. 9 shows velocity contours and velocity vectors in cross-sectional planes in the LPA and the RPA at 2D from the TCPC junction center obtained using CFD for cardiac output (CO) of 6 L/min and SVC/IVC: 50/50. The (a) planes are for baseline TCPC configuration, and (b) planes are for TCPC configuration formed with the present invention (PCAI, 200)

FIG. 9 shows velocity contours in the cross-sectional planes in the LPA and the RPA at 2D from the center of the TCPC junction at the cardiac output (net flow rate) of 6 L/min shared equally by the SVC and the IVC flows. It is interesting to note for the case of the conventional (baseline) TCPC shown in FIG. 9A that the maximum velocity is distributed not in the core but in the annular region around it, suggesting the occurrence of a spiraling flow. The plot of velocity vectors confirms the existence of spiraling flow. However, for the TCPC case with the present invention, Pulmonary Circulation Assist Implant, two high-velocity cores are seen in FIG. 9B emerging from the corner flows formed by the Flow Manipulator and the junction walls. The velocity distribution appears nearly symmetric about the plane of the Flow Manipulator and about the midplane normal to the Flow Manipulator. The plot of velocity vectors illustrates diminished swirling flow with the indiscernible pattern.

Figure 10:
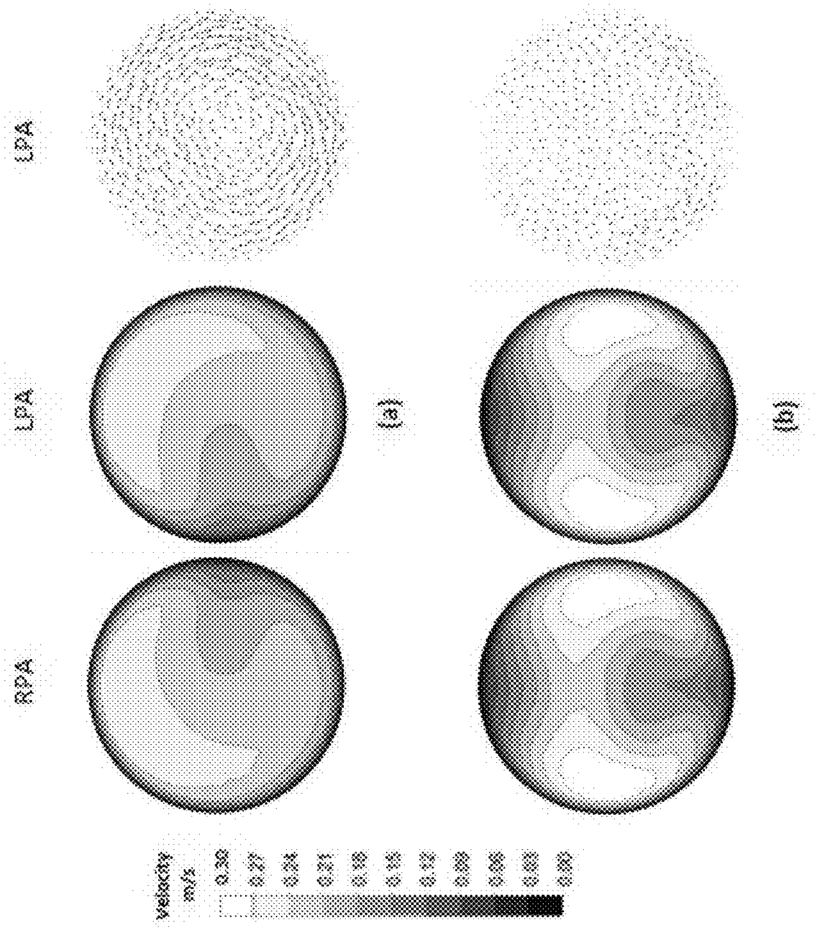
FIG. 10 shows velocity contours and velocity vectors in cross-sectional planes in the LPA and the RPA at 2D from the TCPC junction center obtained using CFD for cardiac output (CO) of 6 L/min and SVC/IVC: 30/70. The (a) planes are for baseline TCPC configuration, and planes (b) are for TCPC configuration formed with the present invention (PCAI, 200)

FIG. 10A-B shows velocity contours in the cross-sectional planes in the LPA and the RPA at 2D from the center of the TCPC junction at the cardiac output (net flow rate) of 6 L/min shared proportionately 30% by the SVC flow and 70% by the IVC flow. Such a proportion of the caval flows in TCPC patients normally occurs during physical exercise. The conventional (baseline) TCPC presents unusual flow features wherein the high-speed flow from the IVC rotates due to the swirl and occupies the upper region of low-speed flow from the SVC as seen in FIG. 10A. The plot of velocity vectors shows a strongly swirling flow whose axis is somewhat displaced from the center. In contrast, FIG. 10B shows that the present invention eliminates the swirl in the flow and exhibits the symmetry in the flow about the plane normal to that of the Flow Manipulator.

Figure 11A:
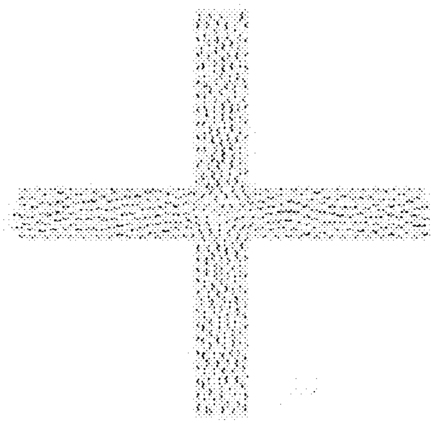
FIG. 11A illustrates the velocity vector field obtained using CFD for the cardiac output (CO) of 6 L/min in the midplane of baseline TCPC configuration for SVC/IVC: 50/50.
Figure 11B:
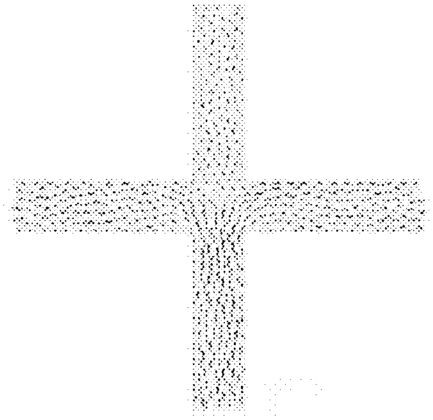
FIG. 11B illustrates the velocity vector field obtained using CFD for the cardiac output (CO) of 6 L/min in the midplane of baseline TCPC configuration for SVC/IVC: 30/70.
Figure 11C:
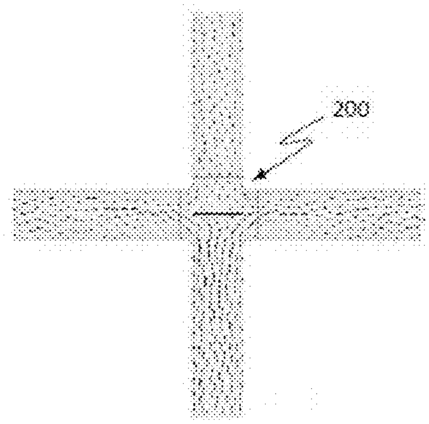
FIG. 11C illustrates the velocity vector field obtained using CFD for the cardiac output (CO) of 6 L/min in the midplane of TCPC configuration formed with the present invention (PCAI, 200) for SVC/IVC: 30/70.

The occurrence of retrograde flow is an undesirable phenomenon in the vascular flow system. FIG. 11A-C shows details of the velocity vector fields in the mid-transverse plane of the TCPC configuration for the cardiac output (net flow rate) of 6 L/min. For the SVC and the IVC flow rates being equal, the stagnation point due to their collision forms in the center of the TCPC junction as seen in FIG. 11A. But for the increasing IVC flow rate, the stagnation point is pushed towards the SVC, and as the gap closes, it results in retrograde flow. FIG. 11B demonstrates this phenomenon through the velocity vector plot obtained for 70% contribution from the IVC flow. When the present invention, Pulmonary Circulation Assist Implant 200, is used to form the TCPC configuration, it completely suppresses the retrograde flow for the 70% contribution from the IVC flow with high velocity by forcing the stagnation points to stay on both the surfaces of the Flow Manipulator as shown in FIG. 11C. Since the stagnation points are fixed on the Flow Manipulator regardless of the momentum difference between the SVC flow and the IVC flow, the possibility of the retrograde flow is nil even when a pump is required to augment the caval flow pressure.

Figure 12A:
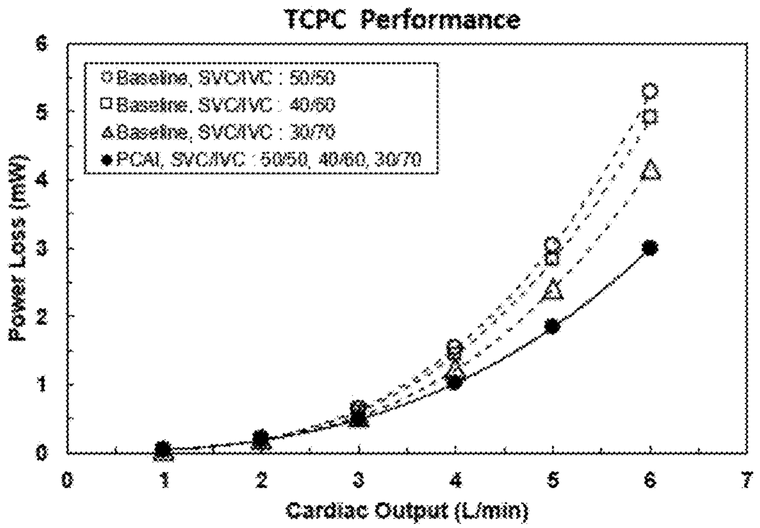
FIG. 12A depicts a plot of power loss encountered by TCPC configuration of an adult at various cardiac outputs for different SVC to IVC flow ratios.

Power requirement for the blood circulation in the cardiovascular system is an important parameter, even more so for a TCPC patient having a univentricular heart which is also required to support the additional workload of pulmonary circulation. The power in the vascular system blood flow, at any diametrical plane, can be estimated from the product of the total pressure and the flow rate. The power loss in the blood flow across the TCPC junction is the difference between the combined power in the SVC flow and IVC flow at the entrance of the TCPC junction and the combined power in the LPA flow and the RPA flow at the exit of the TCPC junction. The power loss, thus estimated from the calculation of power in the planes at 2D from the center of the TCPC junction for various cardiac outputs (net flow rates) comprised of different contributions from the SVC and the IVC flows, is shown in FIG. 12A for a case of an adult patient. The power loss increases non-linearly with the flow rate. The rate of power loss for the baseline is seen to decrease with an increasing proportion of the IVC flow. However, what is surprising to note for the TCPC configuration formed by the present invention, Pulmonary Circulation Assist Implant (PCAI 200), is that the power loss is insensitive to the variation in the proportion of the SVC flow and the IVC flow, as a result, all the curves collapse onto each other much below those of the baseline. Reduction in cardiovascular power loss is physiologically crucial for the functional single ventricle in a TCPC patient as it also supports an additional load of pulmonary circulation. The power-saving from the present invention, the Pulmonary Circulation Assist Implant (PCAI 200), is quantified from the difference between the power losses suffered by the baseline TCPC and the present invention (PCAI 200). The power saving thus obtained is plotted against the cardiac output (net flow rate) in FIG. 12B. It shows that only marginal gains are achievable at low flow rates. The power-saving increases monotonically, but with the declining rate with the increase in the cardiac output. The power-saving curves show dependence on the proportions of the SVC flow and the IVC flow. When the SVC flow and the IVC flow are in equal proportions, a maximum power-saving of 44% is achievable at the cardiac output of 6 L/min, which reduces to 23% when the IVC flow shares 70% of the cardiac output. Thus, the implantation of the present invention, Pulmonary Circulation Assist Implant (PCAI 200), for the TCPC procedure has inherent advantages of proportionate distribution of the SVC flow and the IVC flow to both the lungs and reduced power loss.

Figure 12B:
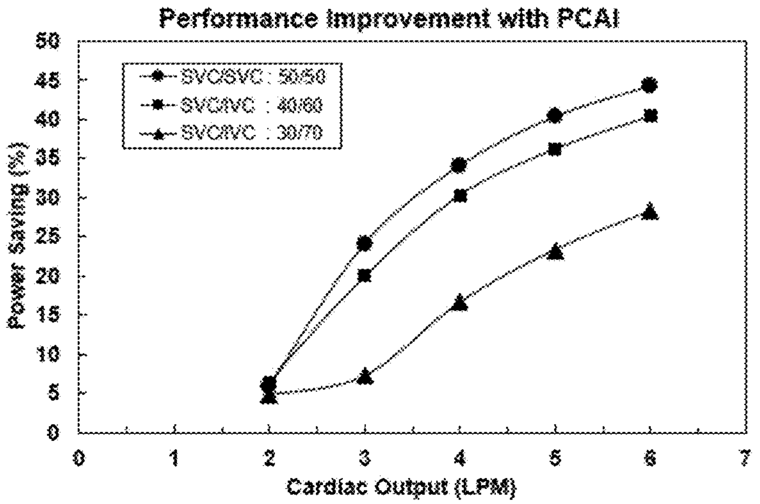
FIG. 12B depicts a plot of saving in power due to the present invention (PCAI, 200)
Figure 13A:
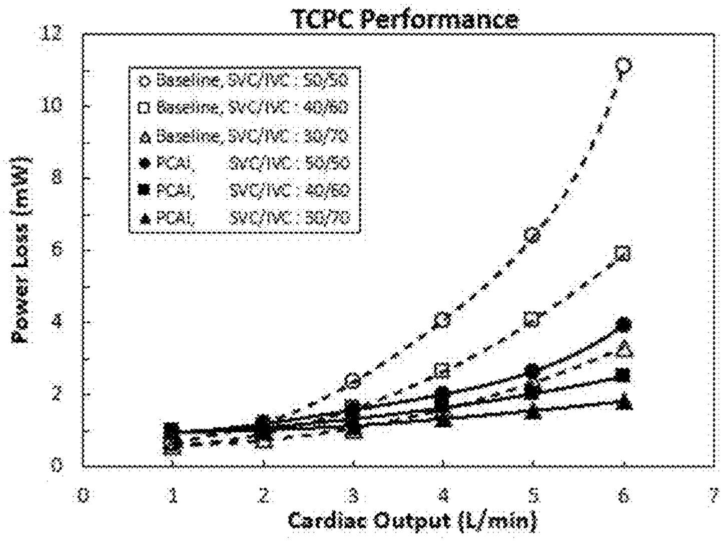
FIG. 13A depicts a plot of power loss encountered by TCPC configuration of a child at various cardiac outputs for different SVC to IVC flow ratios.
Figure 13B:
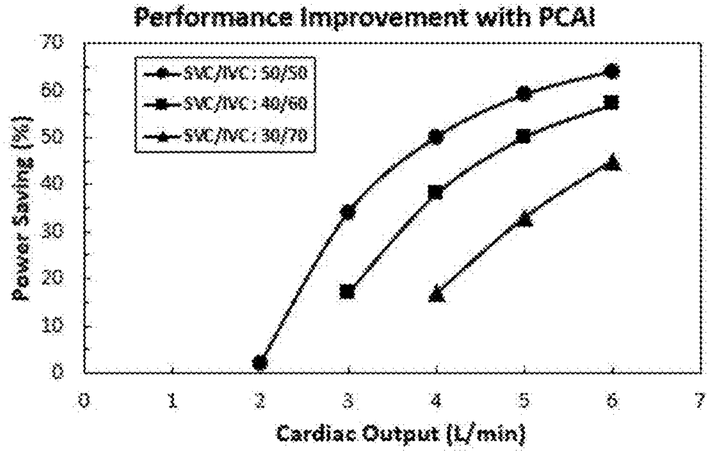
FIG. 13B depicts a plot of saving in power due to the present invention (PCAI, 200)

In the TCPC procedure for a child, despite the SVC and RPA being small in size, the prosthetic conduit of 18 mm diameter is normally used for the IVC as a standard practice followed by most cardiac surgeons. Therefore, a Pulmonary Circulation Assist Implant geometry was designed to examine the influence of SVC, RPA, and LPA with reduced diameters (12 to 14 mm) appropriate to a child in combination with the IVC diameter of 18 mm. Power loss obtained by a numerical simulation of flow through a TCPC configuration prepared with this PCAI for a child is shown in FIG. 13A. The baseline TCPC suffers nearly double power loss in comparison with an adult for the IVC flow contributing 50% of the cardiac output. As the power varies with the cube of the flow velocity, this rise in power loss was expected due to enhanced flow velocity caused by the reduced diameter of blood vessels. With a further increase in the share of the IVC flow, a decrease in the SVC flow velocity results in reduced power loss. What is remarkable is the significant reduction in power loss achieved by the application of the present invention, the Pulmonary Circulation Assist Implant (PCAI 200) which changes the phenomenon of the fluid-fluid interaction to the fluid-structure interaction. FIG. 13B shows a plot of the power saving. It is rather surprising to note that though the absolute power loss is higher, the relative power saving is also much higher compared to what is seen in FIG. 12B. This finding can be attributed to the better efficiency of the PCAI design for a child.

Figure 14:
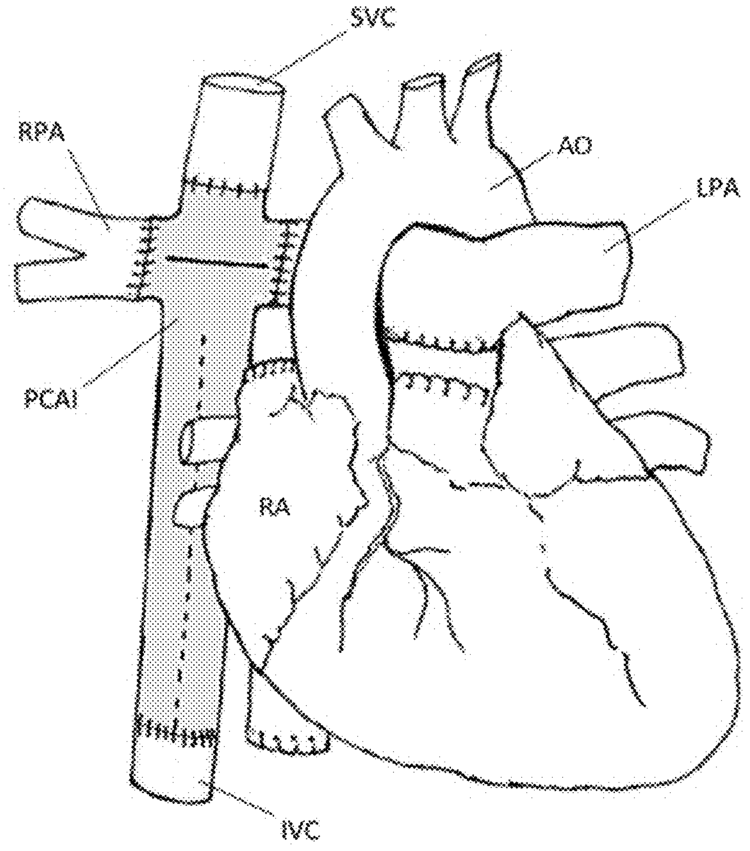
FIG. 14 is a schematic of the surgical implantation of the present invention—Pulmonary Circulation Assist Implant (PCAI, 200)

FIG. 14 schematically illustrates the implantation of the present invention, Pulmonary Circulation Assist Implant (PCAI 200), in an extra-cardiac TCPC configuration. The dotted line printed on the exterior surface of conduit 70 serves to maintain the alignment without any twist while anastomosing to the IVC.

Figure 15A:
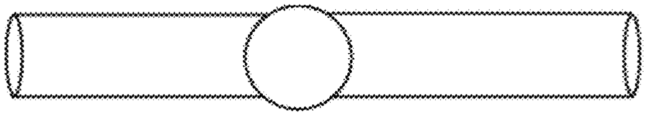
FIG. 15A displays plan views of TCPC configuration without offset depicting planar pulmonary arteries.
Figure 15B:
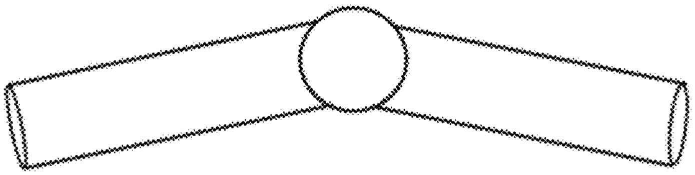
FIG. 15B displays plan views of TCPC configuration without offset depicting non-planar pulmonary arteries.
Figure 15C:
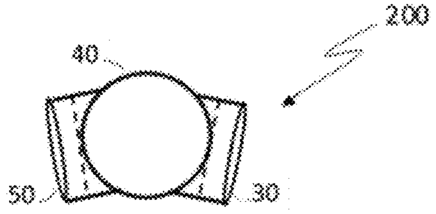
FIG. 15C displays plan views of TCPC configuration without offset depicting the present invention (PCAI, 200) with LPA 30 and RPA 50 ends being non-planar adopted from a more realistic anatomical arrangement.

The TCPC configuration considered herein is, in general, to have the SVC and the IVC in the same plane as depicted in FIG. 15A. However, anatomically the pulmonary artery is non-planar which may result in the form of the TCPC, as shown by the top view in FIG. 15B. The preferred embodiment is capable of adopting the patient-specific geometry. Therefore, the present invention, Pulmonary Circulation Assist Implant (PCAI 200), can be accordingly configured to be non-planar similar to that is schematically shown in FIG. 15C.

The invention claimed is:

1. A Pulmonary Circulation Assist Implant 200 configured to separate bloodstream from an IVC and bloodstream from an SVC to circumvent collision between the bloodstreams without providing an offset, said implant comprising:

- a long conduit 70 crossing an operative transverse short conduit with a junction being formed at said crossing, said long conduit 70 and said short conduit forming a cross,
  - said long conduit 70 having a first open long end 40 and a second open long end 60, with said junction therebetween, said first open long end 40 being configured to be anastomosed with a Superior Vena Cava (SVC), said second open long end 60 being configured to be anastomosed with an Inferior Vena Cava (IVC);
  - said short conduit having a first open short end 30 and a second open short end 50, with said junction therebetween, said first open short end 30 being configured to be anastomosed with a Left Pulmonary Artery (LPA), said second open short end 50 being configured to be anastomosed with a Right Pulmonary Artery (RPA); and
- a flow manipulator 100 being provided at said junction, said flow manipulator 100 configured to, smoothly, regulate blood flows from said Superior Vena Cava (SVC) and said Inferior Vena Cava (IVC) to said Left Pulmonary Artery (LPA) and said Right Pulmonary Artery (RPA), respectively, by forming four distinct quadrants, for smooth curvilinear flows of blood streams entering through said ends 40, 60 of said long conduit and exiting through said ends 30, 50 of said short conduit.

2. The Pulmonary Circulation Assist Implant 200 as claimed in claim 1 wherein, said implant being made of compliant and biocompatible materials having long term hemocompatibility properties.

3. The Pulmonary Circulation Assist Implant 200 as claimed in claim 1 wherein, said long conduit 70, having a diameter between 18 and 20 mm, forming a prosthetic extension of said Inferior Vena Cava (IVC).

4. The Pulmonary Circulation Assist Implant 200 as claimed in claim 1 wherein, said first open short end 30 and a second open short end 50 being sized in the range (10 to 16 mm) of said Right Pulmonary Artery (RPA) diameter.

5. The Pulmonary Circulation Assist Implant 200 as claimed in claim 1 wherein, said first open long end 40 being sized in the range (10 to 16 mm) of said Superior Vena Cava (SVC) diameter.

6. The Pulmonary Circulation Assist Implant 200 as claimed in claim 1 wherein, said second open long end 60 being larger in diameter than said first open long end 40.

7. The Pulmonary Circulation Assist Implant 200 as claimed in claim 1 wherein, said flow manipulator 100 being a stiff flat element having a smooth surface finish, said flow manipulator 100 being positioned in a plane defined by a locus of points formed by a spaced apart region between:

a centre plane defined across a flow axis, of said short conduit; and 0.1 times the diameter of said second open long end 60.

8. The Pulmonary Circulation Assist Implant 200 as claimed in claim 1 wherein, said flow manipulator 100 being a stiff flat element having a smooth surface finish, said flow manipulator 100 being positioned in a plane defined by a locus of points formed by a spaced apart region between:

a centre plane defined across a flow axis, of said short conduit; and 0.1 times the diameter of said second open long end 60, in that, said flow manipulator 100 being positioned, offset, operatively towards said first open long end 40.

9. The Pulmonary Circulation Assist Implant 200 as claimed in claim 1 wherein, said flow manipulator 100 spans said junction wherein operative lateral sides of said flow manipulator 100 connect normally with inner curved opposite walls in order to hold said flow manipulator 100, in position, making two longitudinal corners within said formed junction of said implant 200.

10. The Pulmonary Circulation Assist Implant 200 as claimed in claim 1 wherein, said flow manipulator 100 spans said junction wherein operative end free trailing edges 13, 15 of said flow manipulator 100 extending, covering fully, projected opening of said ends 40 and 60, and facilitating merging and coflowing of streams from said Superior Vena Cava (SVC) and from said Inferior Vena Cava (IVC) flowing through said Left Pulmonary Artery (LPA) and said Right Pulmonary Artery (RPA).

11. The Pulmonary Circulation Assist Implant 200 as claimed in claim 1 wherein, width of said flow manipulator 100 matches diameter of said second open long end 60.

12. The Pulmonary Circulation Assist Implant 200 as claimed in claim 1 wherein, joints of said junction of said long conduit and said short conduit are rounded off to render curved corners 21 and 22 for smooth turning of flows, at said junction, caused by said flow manipulator 100, without separation.

13. The Pulmonary Circulation Assist Implant 200 as claimed in claim 1 wherein, axis of said short conduit being a curvilinear axis matching a patient's Right Pulmonary Artery (RPA).

14. The Pulmonary Circulation Assist Implant 200 as claimed in claim 1 wherein, axis of said short conduit being a non-planar curvilinear axis matching a patient's Right Pulmonary Artery (RPA).

* * * * *